United States Patent
Murashita

(10) Patent No.: US 8,202,220 B2
(45) Date of Patent: *Jun. 19, 2012

(54) ULTRASOUND DIAGNOSTIC APPARATUS

(75) Inventor: Masaru Murashita, Tokyo (JP)

(73) Assignee: Hitachi Aloka Medical, Ltd., Tokyo (JP)

( * ) Notice: Subject to any disclaimer, the term of this patent is extended or adjusted under 35 U.S.C. 154(b) by 725 days.

This patent is subject to a terminal disclaimer.

(21) Appl. No.: 12/174,123

(22) Filed: Jul. 16, 2008

(65) Prior Publication Data

US 2009/0024029 A1 Jan. 22, 2009

(30) Foreign Application Priority Data

Jul. 17, 2007 (JP) ................................. 2007-185565

(51) Int. Cl.
*A61B 8/00* (2006.01)
*A61B 8/06* (2006.01)
(52) U.S. Cl. .................... 600/443; 600/454; 128/916
(58) Field of Classification Search .................. 600/407, 600/437, 443–448, 453–456; 128/916; 382/131, 382/254, 260–265
See application file for complete search history.

(56) References Cited

U.S. PATENT DOCUMENTS

| | | | |
|---|---|---|---|
| 5,474,073 A | 12/1995 | Schwartz et al. | |
| 5,602,891 A * | 2/1997 | Pearlman | ........................ 378/62 |
| 5,647,360 A * | 7/1997 | Bani-Hashemi et al. | ..... 600/425 |
| 5,879,302 A | 3/1999 | Hashimoto et al. | |
| 6,102,864 A * | 8/2000 | Hatfield et al. | ............... 600/454 |
| 6,126,603 A | 10/2000 | Hatfield et al. | |
| 6,249,693 B1 | 6/2001 | Cline et al. | |
| 6,312,385 B1 | 11/2001 | Mo et al. | |
| 6,322,509 B1 * | 11/2001 | Pan et al. | ...................... 600/443 |
| 6,334,847 B1 | 1/2002 | Fenster et al. | |
| 6,352,509 B1 | 3/2002 | Kawagishi et al. | |
| 6,423,006 B1 | 7/2002 | Banjanin | |
| 6,438,403 B1 | 8/2002 | Cline et al. | |
| 6,503,202 B1 | 1/2003 | Hossack et al. | |
| 6,547,731 B1 | 4/2003 | Coleman et al. | |
| 2003/0097068 A1 * | 5/2003 | Hossack et al. | ............... 600/443 |
| 2006/0184021 A1 * | 8/2006 | Kim et al. | ..................... 600/437 |

(Continued)

FOREIGN PATENT DOCUMENTS

EP 1152364 A2 11/2001

(Continued)

OTHER PUBLICATIONS

European Search Report dated Sep. 2, 2010, issued in corresponding European Patent Application No. 08012536.2.

(Continued)

*Primary Examiner* — Francis Jaworski
(74) *Attorney, Agent, or Firm* — Westerman, Hattori, Daniels & Adrian, LLP

(57) ABSTRACT

An ultrasound diagnostic apparatus which forms a three-dimensional bloodstream image by reference to volume data obtained from a three-dimensional space within a living organism. Binarization processing and three-dimensional labeling processing are applied to velocity volume data, to thereby generate three-dimensional mask data. At this time, because a bloodstream object has a larger volume size than a noise object, this difference in volume size is utilized to discriminate between a bloodstream portion and a noise portion. Bloodstream volume data are then generated from the velocity volume data and by reference to the three-dimensional mask data. Then, a three-dimensional bloodstream image is formed by reference to the bloodstream volume data.

16 Claims, 4 Drawing Sheets

U.S. PATENT DOCUMENTS

| | | |
|---|---|---|
| 2006/0184029 A1 | 8/2006 | Haim et al. |
| 2008/0009727 A1* | 1/2008 | Kataguchi ............... 600/437 |
| 2009/0024033 A1* | 1/2009 | Murashita ............... 600/443 |

FOREIGN PATENT DOCUMENTS

| | | |
|---|---|---|
| EP | 1189074 A2 | 3/2002 |
| JP | 10-171976 A | 6/1998 |
| JP | 2000-210289 A | 8/2000 |
| JP | 2000-237192 A | 9/2000 |
| JP | 2001-17428 A | 1/2001 |
| JP | 2002-052026 A1 | 2/2002 |
| JP | 2004-215701 A | 8/2004 |
| JP | 2005-40622 A | 2/2005 |
| JP | 2005-157664 A | 6/2005 |
| JP | 2006-51202 A | 2/2006 |
| WO | 2006/086442 A2 | 8/2006 |

OTHER PUBLICATIONS

Partial European Search Report, issued May 12, 2010 for corresponding European Patent Application No. 08012536.2.

McInerney, Tim et al.; "Deformable Models in Medical Image Analysis"; Proceedings of the IEEE Workshop on Mathematical Methods in Biomedical Image Analysis, Jun. 21, 1995, p. 171-180.

Bullitt, Elizabeth et al.; "Volume Rendering of Segmented Tubular Objects"; Lecture Notes in Computer Science 2208, Jan. 1, 2001, p. 161-168.

Partial European Search Report, issued May 17, 2010 for corresponding European Patent Application No. 08012537.0.

Mroz, Lukas et al.; "Maximum Intensity Projection at Warp Speed"; Computers and Graphics, Jun. 1, 2000, p. 343-352, vol. 24 No. 3.

European Search Report dated Apr. 29, 2011, issued in corresponding European Patent Application No. 08012537.0.

Chinese Office Action dated May 20, 2011, issued in corresponding Chinese Patent Application No. 200810128370.8.

Japanese Notice of Grounds for Rejection dated Feb. 21, 2012, issued in corresponding Japanese Patent Application No. 2007-185565.

European Office Action dated Jul. 13, 2011, issued in corresponding European Patent Application No. 08012536.2.

* cited by examiner

ULTRASOUND DIAGNOSTIC APPARATUS

BACKGROUND

1. Technical Field

The present invention relates to an ultrasound diagnostic apparatus, and more particularly to a technology of forming a three-dimensional bloodstream image.

2. Related Art

In the medical field, an ultrasound diagnostic apparatus transmits and receives ultrasonic waves to and from a living organism and generates an ultrasound image on the basis of a reception signal obtained by transmission and reception of the ultrasonic waves. Typical ultrasound images may include a two-dimensional tissue image, which is a monochrome image (B-mode image), and a two-dimensional bloodstream image, which is a color image. A two-dimensional bloodstream image is color representation of Doppler components or motion information (e.g., velocity information, power information, and so on) which are contained in a reception signal. A two-dimensional tissue image may be formed by reference to the motion information. In general, a two-dimensional tissue image and a two-dimensional bloodstream image are combined to form a combined image, which is then to be displayed on a display.

In recent years, three-dimensional ultrasound diagnostic apparatuses which form a three-dimensional tissue image by reference to volume data obtained by transmission and reception of ultrasonic waves with respect to a three-dimensional space within a living organism have been in wide-spread use. Conventionally, a three-dimensional tissue image is formed by using a volume rendering method, for example, and is a stereoscopic representation of a tissue (e.g. an organ) within a living organism. Meanwhile, motion volume data can be obtained by extracting motion information from volume data. Here, motion volume data refers to three-dimensional data formed of the motion information. By applying three-dimensional image processing to the motion volume data, a three-dimensional bloodstream image can be formed.

JP 2005-157664 A (Reference 1), JP 2005-40622 A (Reference 2), JP 2006-51202 A (Reference 3), and JP 2001-17428 A (Reference 4) disclose conventional ultrasound diagnostic apparatuses which form a three-dimensional ultrasound image.

The motion volume data generally contain not only bloodstream data for which image formation is desired but also noises (including clutter) and so on for which image formation is not desired. If a rendering processing is directly applied to the motion volume data containing a great amount of noise to form a three-dimensional bloodstream image, sufficient image quality cannot be achieved in such a three-dimensional bloodstream image. While noises similarly appear in a conventional two-dimensional bloodstream image, disadvantages resulting from appearance of noises on a two-dimensional bloodstream image are not very significant, because these noises were present on a scan plane which is a two-dimensional plane. In a three-dimensional bloodstream image, on the other hand, noises which are present over the whole three-dimensional space are imaged. Consequently, if a great amount of noise appears around and in front and back portions of a bloodstream on a three-dimensional bloodstream image, these noises obstruct observation of the bloodstream. Here, the amount of noise within a three-dimensional space is several tens to several hundreds times as much as that present on a two-dimensional plane.

SUMMARY

The present invention advantageously provides an ultrasound diagnostic apparatus which forms a three-dimensional bloodstream image in which noises are effectively removed or reduced.

In accordance with one aspect of the present invention, there is provided an ultrasound diagnostic apparatus, comprising a unit which transmits and receives ultrasonic waves with respect to a three-dimensional space within a living organism to obtain original volume data, a computation unit which extracts motion information from the original volume data to generate motion volume data, an identification unit which specifies a plurality of objects included in the motion volume data and identifies a type of each of the objects which are specified to generate identification data, an extraction unit which extracts bloodstream volume data from the motion volume data by reference to the identification data, and an image-forming unit which forms a three-dimensional bloodstream image by reference to the bloodstream volume data. Preferably, the identification unit identifies the type of an object by reference to the size of each of the objects which are specified.

With the above structure, the motion information contained in the original volume data is extracted and the motion volume data which are formed of the extracted motion information are generated. The motion information may include a velocity, an absolute value of a velocity, a power, and so on, which are computed from Doppler components. The motion information may be Doppler information, or two-dimensional or three-dimensional vector information. The identification unit generates identification data by reference to the motion volume data. More specifically, the identification unit has a function of specifying each object, a function of identifying a type of each object, and so on. While use of three-dimensional labeling processing is desired for specification of the objects, other processing operations may be used. When the three-dimensional labeling processing is adopted, it is desirable to apply a preliminary processing (i.e. invalid voxel removing processing such as binarization processing) to the motion volume data prior to the three-dimensional labeling processing. An object is generally a spatial mass (an aggregate of spatially contiguous voxels) existing within a three-dimensional space, and corresponds either to bloodstream or noise when roughly categorized. Noise may include clutter. An object composed of a single voxel may be specified. As, in general, a bloodstream object has a large size whereas a noise object has a small size, it is desirable to identify the object type with reference to the object size. In this manner, whether or not each object is a bloodstream can be identified. At the time of this identification, in addition to or in place of the object size, other information including the shape of an object, statistical values concerning the velocities and powers, and so on may be considered. Once the types of the individual objects are identified, resulting identification data are generated. The identification data are desirably three-dimensional mask data, which are three-dimensional reference data which mask (exclude) noise portions in the motion volume data or which extract bloodstream portions in the motion volume data. With the use of the identification data, bloodstream volume data are generated from the motion volume data. Then, the three-dimensional rendering processing is applied to the bloodstream volume data to thereby form a three-dimensional bloodstream image. The final three-dimensional bloodstream image, which contains no noise or only a slight amount of noise, can represent the running state of a bloodstream clearly, so that image information which is useful for diagnosis of diseases can be provided. In this three-dimensional bloodstream image, bloodstreams are preferably represented in colors, and are represented in different colors in accordance with the direction of flow, as required.

Preferably, the identification unit further includes a labeling-processing unit which applies three-dimensional labeling processing to the motion volume data to specify the plurality of objects. The three-dimensional labeling processing is a processing operation for identifying and specifying as a single object an aggregate of spatially contiguous voxels having the same attribute. In general, an object number is assigned to each object, and the number of voxels forming an object is counted. However, various other identification methods may be adopted, so long as the individual objects can be specified. Further, it is also possible to set a three-dimensional region of interest to thereby restrict a three-dimensional range to be imaged or a three-dimensional range to be subjected to the labeling processing.

Preferably, the identification unit further includes a determination unit which determines whether or not each object is a bloodstream, by reference to a three-dimensional volume size of each object. As a blood vessel has an elongated shape within a three-dimensional space, even a thin blood vessel generally has a certain degree of volume size. In contrast, noise (clutter) has a relatively smaller volume size. Accordingly, it is possible to determine whether or not each object is a bloodstream (or whether or not each object is noise) by using a three-dimensional volume size as a determination criteria. Here, in addition to or in place of the volume size, other information may be referred to.

Preferably, the three-dimensional volume size is the number of voxels which is counted in the three-dimensional labeling processing. As described above, as the number of voxels is automatically counted when extracting the individual objects in the labeling processing, this counting result is used in the following step.

Preferably, the identification unit further includes a binarization processing unit which applies binarization processing to the motion volume data prior to the three-dimensional labeling processing, and the volume data having been subjected to the binarization processing are input to the labeling processing unit. As the labeling processing is directed at identification of candidate bloodstream, it is desirable to previously exclude voxels which are not considered to be candidates of bloodstream from among the subjects of processing. For this reason, binarization processing is applied. Here, while, in a sense, the binarization processing is also aimed at removing noises, with the binarization processing, discrimination in voxel units is performed by reference to the magnitude of motion information (e.g. a velocity, a power, and so on). In contrast, with the labeling processing and the determination processing described above, a noise which is difficult to distinguish from a bloodstream by reference to the magnitude of motion information is identified by reference to the size of an object volume.

Preferably, the binarization processing unit compares each of voxel data items forming the motion volume data with a discrimination reference value to convert each of voxel data items into a valid value or an invalid value. The valid value represents a candidate bloodstream voxel, and the invalid value represents a voxel which is not a bloodstream candidate. This binarization processing may also serve as a known wall motion filter (i.e. a removal filter of a low-velocity motion), or such a filter may be provided separately.

Preferably, the identification unit identifies an object which is greater than a predetermined size as a bloodstream and identifies an object which is smaller than the predetermined size as noise which is not a bloodstream. It is desirable to variably set the predetermined size in accordance with a subject of ultrasound diagnosis, the size of a three-dimensional region or a three-dimensional region of interest, and other conditions.

Preferably, the identification data are three-dimensional mask data which are used for extracting a bloodstream portion in the motion volume data or for excluding a noise portion in the motion volume data. For example, by performing a logical operation in units of voxels between the three-dimensional mask data and the motion volume data, the bloodstream volume data can be generated.

Preferably, the image-forming unit sets a plurality of rays with respect to the bloodstream volume data to determine a pixel value based on a sequence of voxel data on each ray. Various methods may be used for forming a three-dimensional bloodstream image by reference to the bloodstream volume data. For example, a maximum value method, a volume rendering method in which opacity is used, a surface rendering method, and so on may be used.

Preferably, the image-forming unit determines a pixel value concerning each ray by means of a maximum value method. Preferably, the image-forming unit assumes a first peak on each ray as a maximum value. Preferably, the first peak corresponds to a velocity or a power at a center portion of a bloodstream located on the front side closest to a viewpoint. As such, when one bloodstream on the front side and the other bloodstream on the further back side cross each other, the bloodstream on the front side is always represented preferentially. Even if the bloodstream on the back side is a high-speed bloodstream, as the bloodstream on the back side is not allowed to be displayed preferentially, the image can retain a sense of depth. If weighting in the depth direction is applied so as to prevent preferential display of the high-speed bloodstream on the back side, the velocity of the bloodstream cannot be represented accurately. With the above structure, however, such disadvantages can be prevented.

In accordance with another aspect of the present invention, there is provided an image-processing program to be executed in a computer, for forming a three-dimensional bloodstream image by reference to motion volume data, the image-processing program comprising a module which specifies a plurality of objects included in the motion volume data and determines whether or not each of the objects which are specified is a bloodstream to thereby generate identification data, a module which extracts bloodstream volume data from the motion volume data by reference to the identification data, and a module which forms a three-dimensional bloodstream image by reference to the bloodstream volume data. Each module described above corresponds to a specific software function or a program portion which implements the specific function. The program according to the present invention is provided via a storage medium or via the network serving as a medium and is then installed in a computer. The storage medium may be a medium such as a CD-ROM. Here, the above computer is a general personal computer or an ultrasound diagnostic apparatus, for example. A three-dimensional bloodstream image may be formed by reference to the volume data which are obtained in real time or by reference to the volume data which are stored.

BRIEF DESCRIPTION OF THE DRAWINGS

A preferred embodiment of the present invention will be described in detail by reference to the following figures, wherein.

DETAILED DESCRIPTION

A preferred embodiment of the present invention will be described in detail with reference to the accompanying drawings.

Figure 1:
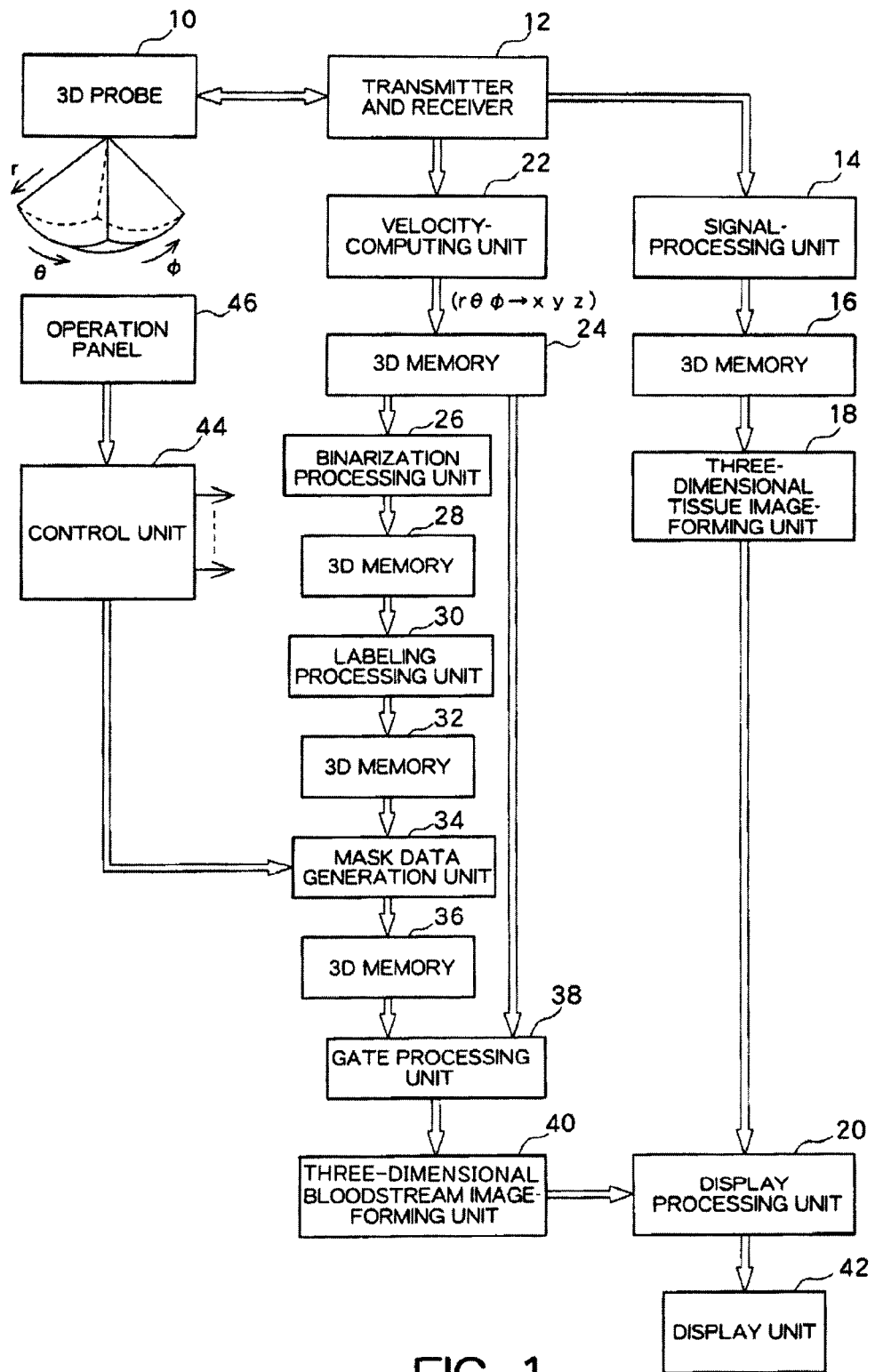
FIG. 1 is a block diagram showing an ultrasound diagnostic apparatus according to a preferred embodiment of the present invention.

FIG. 1 is a block diagram showing the overall structure of an ultrasound diagnosis apparatus according to a preferred embodiment of the present invention. The ultrasound diagnostic apparatus according to the present embodiment is for use in the medical field, and includes a function of forming a three-dimensional bloodstream image which is a stereoscopic representation of bloodstream within a living organism.

In the present embodiment, a 3D (three-dimensional) probe 10 includes a 2D (two-dimensional) array transducer. The 2D array transducer includes a plurality of transducer elements which are arranged two-dimensionally. An ultrasound beam is formed by the 2D array transducer and is electronically scanned. Known electronic scan methods include electronic sector scan, electronic linear scan, and others. In FIG. 1, a symbol "r" indicates the depth direction, which corresponds to the ultrasound beam direction. Symbols "θ" and "φ" represent directions in which an ultrasound beam is scanned. In the illustrated example, a pyramid-shaped echo data acquisition region, which is a three-dimensional space constructed within a living organism, is formed. Here, in place of the 2D array transducer, a 1D array transducer and a mechanism for mechanically scanning the 1D array transducer may be provided.

A unit 12 functions as a transmitting beam former transmitter and a receiving beam former receiver. The unit 12, at the time of transmission, provides a plurality of transmission signals, in parallel, to the 2D array transducer, thereby forming a transmitting beam. At the time of reception, a reflection wave from within the living organism is received by the 2D array transducer, which outputs a plurality of reception signals, in parallel, to the unit 12. The unit 12 then performs phase adjustment and summation processing with respect to the plurality of reception signals to thereby electronically form a receiving beam. In this case, a reception dynamic focus technology is applied. According to the present embodiment, the reception signal (beam data) having been subjected to beam adjustment and summation is output to a signal-processing unit 14 and a velocity-computing unit 22. Here, an ultrasound beam for forming a three-dimensional tissue image and an ultrasound beam for forming a three-dimensional bloodstream image may be formed separately.

The signal-processing unit 14 is a module which executes signal processing for forming a three-dimensional tissue image, and has functions such as detection processing, logarithmic compression processing, and so on. The beam data having been subjected to the signal processing are stored in a 3D memory 16. Here, when storing and reading data with respect to the 3D memory 16, coordinate transformation processing is executed. In the present embodiment, a three-dimensional tissue image-forming unit 18 forms a three-dimensional tissue image from volume data stored in the 3D memory 16, by means of a volume rendering method in which opacity is used. More specifically, a plurality of rays are set with respect to the volume data, and, for each ray, a voxel computation is sequentially repeated along the ray to thereby determine a pixel value. The image data of the three-dimensional tissue image are output to a display processing unit 20. The image data are then provided to a display unit 42, which displays the three-dimensional tissue image.

Now, processing for forming a three-dimensional bloodstream image will be described in detail. The three-dimensional bloodstream image is displayed separately from or in combination with the three-dimensional tissue image described above.

The velocity-computing unit 22, in the present embodiment, includes a quadrature detector, a low-velocity motion removal filter, an autocorrelation operator, a velocity operator, and so on. Specifically, the velocity-computing unit 22 has a function of computing the velocity information as one type of motion information contained in a reception signal. More specifically, the velocity-computing unit 22 extracts Doppler components contained in a reception signal, applies an autocorrelation operation with respect to the Doppler components, and further computes the velocity (the average velocity) from the autocorrelation result. The velocity which is obtained in this case has a positive or negative sign. The velocity information is computed for each voxel. Although the velocity is obtained as the motion information in the present embodiment, a power (or an absolute value of the velocity) may be computed. Further, although in the present embodiment the velocity information along the beam direction is obtained, a two-dimensional velocity vector or a three-dimensional velocity vector may be computed.

The velocity data output from the velocity-computing unit 22 are stored in a 3D memory 24. Then, when writing or reading the data with respect to the 3D memory 24, coordinate transformation is executed. In this case, coordinate transformation from the rθφ coordinate system to the XYZ coordinate system is executed. The 3D memory 24 has a storage space corresponding to the three-dimensional space within the living organism described above. The 3D memory 24 stores velocity volume data (motion volume data) formed as an aggregate of velocity data which are voxel data. Here, each of 3D memories 28, 32, and 36, which will be described below, preferably has a storage space similar to that of the 3D memory 24 and functions as a buffer memory.

A binarization processing unit 26 is a module which executes binarization processing with respect to the velocity volume data stored in the 3D memory 24. Specifically, there is executed processing in which a voxel value which is smaller than a predetermined threshold value is replaced with 0 (an invalid value) and a voxel value which is equal to or greater than the predetermined threshold value is replaced with 1 (a valid value). As a result, only the voxel values which are candidates of bloodstreams are specified. The volume data having been subjected to this binarization processing are binary volume data, which are also one type of the motion volume data. The binary volume data are stored in the 3D memory 28.

A labeling processing unit 30 applies three-dimensional labeling processing to the binary volume data, as will be described with reference to FIG. 2. Specifically, the labeling processing unit 30 extracts a voxel aggregation (i.e. an object) having a voxel value 1. In general, a plurality of bloodstreams and a plurality of noises exist within a three-dimensional space, and a plurality of objects are specified as a result of the labeling processing. Each object is composed of a plurality of voxels which are spatially coupled to each other. In this embodiment, these voxels have a voxel value, which is 1. Although an object composed of one isolation voxel may be extracted, such an object is a noise and need not be extracted. Further, the minimum number of voxels forming an object may be defined. Here, the three-dimensional labeling processing itself is a known technology. The volume data having been subjected to the three-dimensional labeling processing or the data of processing results are stored in the 3D memory 32.

Here, with the labeling processing, an object number is assigned to each object, and the number of voxels constituting each object is counted to obtain a count value. The object number and the count value constitute object attribute information.

A mask data generation unit 34 reads out from the 3D memory 32 the volume data and the attribute information obtained as a result of the three-dimensional labeling processing, and executes processing for identifying the type of each object. Namely, the mask data generation unit 34 identifies whether each object is a bloodstream (which is a subject to be imaged) or noise (which is not a subject to be imaged). More specifically, the mask data generation unit 34 compares the number of voxels of each object with a predetermined reference value, and determines an object with the number of voxels which is smaller than the reference value as noise and determines an object with the number of voxels which is equal to or greater than the reference value as a bloodstream. In general, the volume size of noise is smaller than the volume size of a bloodstream within a three-dimensional space. Accordingly, although it is difficult to discriminate noise and bloodstream by reference to the magnitude of velocity, it is possible to distinguish between a noise portion and a bloodstream portion by reference to a difference in the spatial size. For this identification, the count value which is obtained in the three-dimensional labeling processing described above; that is, a volume size, is referred to.

The mask data generation unit 34 generates, for each object, identification data (mask data) representing an identification result of whether the object is a bloodstream or noise. The mask data is three-dimensional volume data, which are reference data which can be used for spatially identifying a portion corresponding to noise and a portion corresponding to a bloodstream.

Here, the mask data which identify an object corresponding to noise can be generated if noise removal is performed in gate processing which will be described below, whereas the mask data which identifies an object corresponding to bloodstream can be generated if extraction of bloodstream is performed in the gate processing. The mask data generated by the mask data generation unit 34 are stored in the 3D memory 36.

A gate-processing unit 38, with the use of the mask data described above, applies bloodstream extraction processing (and/or a noise removal processing) to the motion volume data which are read from the 3D memory 24, and generates, as a result, volume data which basically represent only bloodstreams; i.e., bloodstream volume data, which are then provided to a three-dimensional bloodstream image-forming unit 40.

The three-dimensional bloodstream image-forming unit 40, in the present embodiment, generates a three-dimensional bloodstream image by means of the maximum value method. However, a modified maximum value method is applied in the present embodiment, as will be specifically described below with reference to FIGS. 3 to 5. With the modified maximum value detection method according to the present embodiment, in a portion in which a plurality of bloodstreams cross each other, a bloodstream located on the front side as seen from the viewpoint, which is a bloodstream located closer to the viewpoint, can be represented preferentially, or high-velocity components in the bloodstream can be represented preferentially, so that a clear three-dimensional bloodstream image can be advantageously formed without losing the sense of depth.

The display processing unit 20 has a color processing function, an image-combining function, and so on. The display processing unit 20 outputs image information which is selected in accordance with a display mode set by a user and provides the image information to the display unit 42. In the present embodiment, the three-dimensional tissue image is displayed as a monochrome image, whereas the three-dimensional bloodstream image is displayed as a color image. The three-dimensional bloodstream image is a velocity image in which a bloodstream approaching the probe is represented with red hue and a bloodstream moving away from the probe is represented with blue hue, and also, different velocities are represented by brightness of the respective hues. The display processing unit 20 performs such a coloring processing. As described above, because a bloodstream located on the front side seen from the viewpoint is represented preferentially in a portion in which a plurality of bloodstreams cross each other, problems such as a loss of the sense of depth and unnatural mixture of red and blue colors in a portion where bloodstreams cross each other can be eliminated or alleviated. Also, as a stream with the highest velocity in the center portion of the bloodstream can be represented preferentially due to the method which will be described below, the state of each bloodstream can be advantageously represented in a clear manner.

As a matter of course, the method according to the present invention can be similarly applied to a case in which a power image is displayed as a three-dimensional bloodstream image. A power image is formed as an image of a red color, for example, in which the magnitude of power is represented by brightness. In either case, there can be formed a three-dimensional bloodstream image in which noise, especially undesirable clutter generated due to interference of ultrasonic waves or the like, is effectively reduced.

A control unit 44, which performs operation control of each unit described in FIG. 1, is formed of a CPU and an operation program. An operation panel 46 is connected to the control unit 44. The operation panel 46 includes a keyboard and a trackball and is operated by a user to set the operation conditions and parameters. Here, the function of each of the binarization processing unit 26, the labeling processing unit 30, the mask data generation unit 34, the gate processing unit 38, the three-dimensional image-forming unit 40, the display processing unit 20, and so on, can be essentially implemented as a software function. It is also possible to output the information stored in the 3D memory 24 to an external personal computer and execute the processing described above on the personal computer to thereby form a three-dimensional bloodstream image.

Each of the 3D memories 24 and 16 can be formed as a cine memory having a ring buffer structure. A three-dimensional bloodstream image may be formed as a moving image based on the time-sequential volume data stored over a fixed time period.

Figure 2:
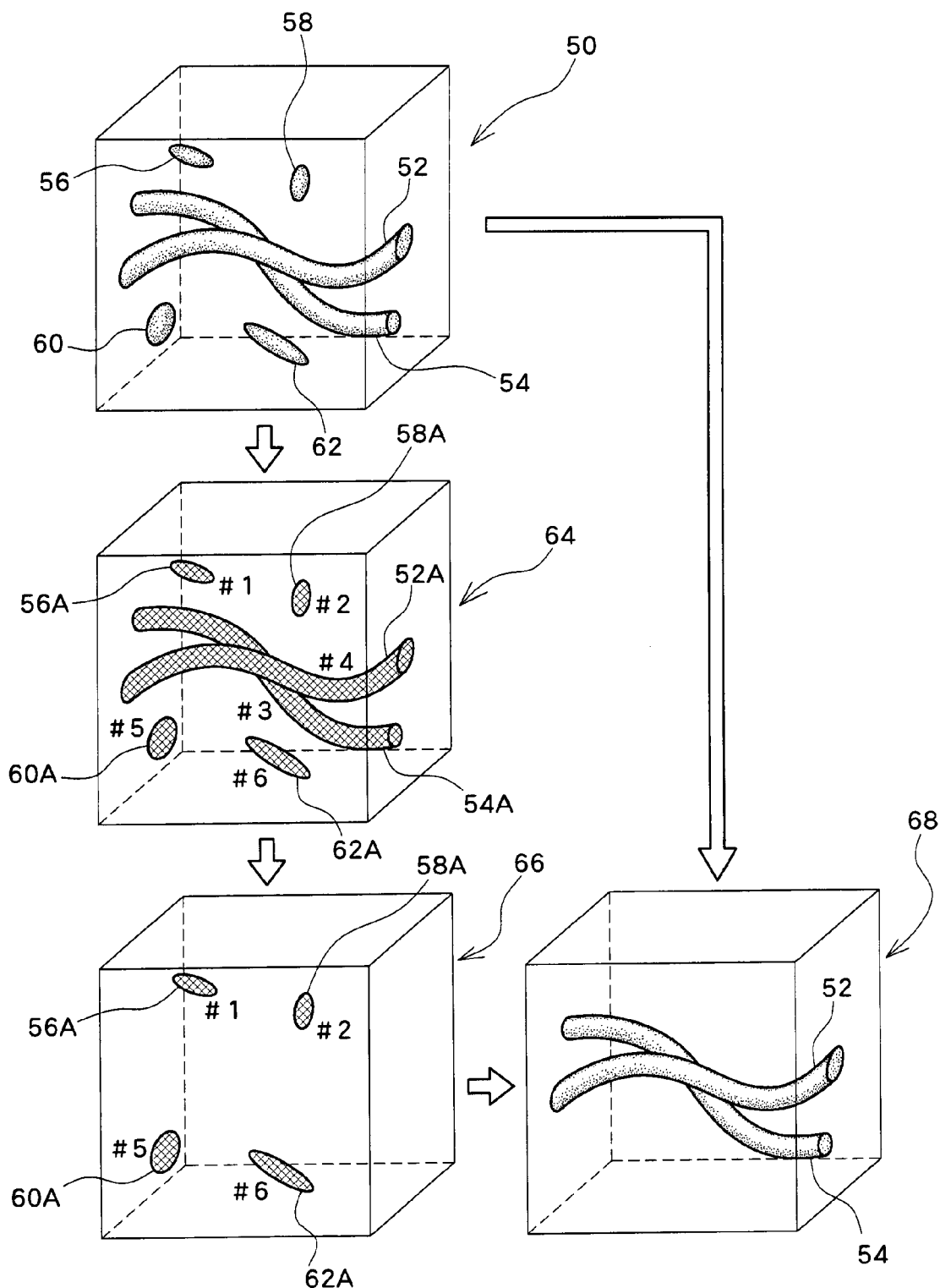
FIG. 2 is a conceptual view for explaining processing for generating bloodstream volume data.

FIG. 2 conceptually shows processing of generating bloodstream volume data. Reference numeral 50 indicates velocity volume data. In this example, portions 52 and 54 corresponding to bloodstreams and portions 56, 58, 60, and 62 corresponding to noises are present within a three-dimensional space.

A result of application of the binarization processing, and then the three-dimensional labeling processing, to the velocity volume data 50 is shown by a view indicated by reference numeral 64. With the binarization processing, a value of 1 is assigned to each voxel forming each of the portions 52, 54, 56, 58, 60, and 62 described above, and a value of 0 is assigned to other voxels. More specifically, in the binarization processing, a predetermined threshold value is set, and a voxel value which is smaller than the threshold value is replaced with 0 and a voxel value which is equal to or greater than the threshold value is replaced with 1, so that a still object and a low-velocity object can be advantageously excluded from the subjects to be processed. As required, various filtering processing operations can be applied to the binarized volume data. Then, with the labeling processing, a plurality of objects 52A, 54A, 56A, 58A, 60A, and 62A which spatially exist are specified. Here, each object is an aggregate of voxels which are spatially contiguous and which have a value 1. An object formed of a single voxel can also be identified. Object numbers #1 to #6 are assigned to the respective objects in a predetermined order. Also, the number of voxels forming each object is counted. Namely, in the three-dimensional labeling processing, at the time of extracting an object, counting of voxels forming the object is executed and the resulting count value is stored as attribute information representing the volume size of the object.

As described above, in view that a bloodstream object generally has a larger volume size whereas a noise object generally has a smaller volume size, it is possible to discriminate between a bloodstream portion and a noise portion. In the example shown in FIG. 2, four noise portions are identified, and these noise portions form three-dimensional mask data 66. In this case, the portions 56A, 58A, 60A, and 62A designated by object numbers #1, #2, #5, and #6, respectively, are specified.

Once the three-dimensional mask data are generated as described above, the three-dimensional mask data 66 are caused to operate on the velocity volume data, and more specifically, a logical operation is performed between the three-dimensional mask data and the velocity volume data, to thereby remove the noise portions 56, 58, 60, and 62 contained in the velocity volume data 50, so that bloodstream volume data 68 in which noise is removed can be generated. The bloodstream volume data 68 basically include only the portions 52 and 54 corresponding to the bloodstreams. Accordingly, by executing rendering processing based on the bloodstream volume data, there can be provided a three-dimensional bloodstream image in which noises are effectively reduced, or the bloodstreams are clearly represented.

Although, in the example shown in FIG. 2, the portions 56A, 58A, 60A, and 62A are identified by the three-dimensional mask data 66 as the subjects to be excluded, various other methods may also be applied for configuring the three-dimensional mask data 66. For example, three-dimensional mask data for extracting the bloodstream portions may be configured. In any case, control data which can be used for achieving removal of noise portions and extraction of bloodstream portions are generated.

Figure 3:
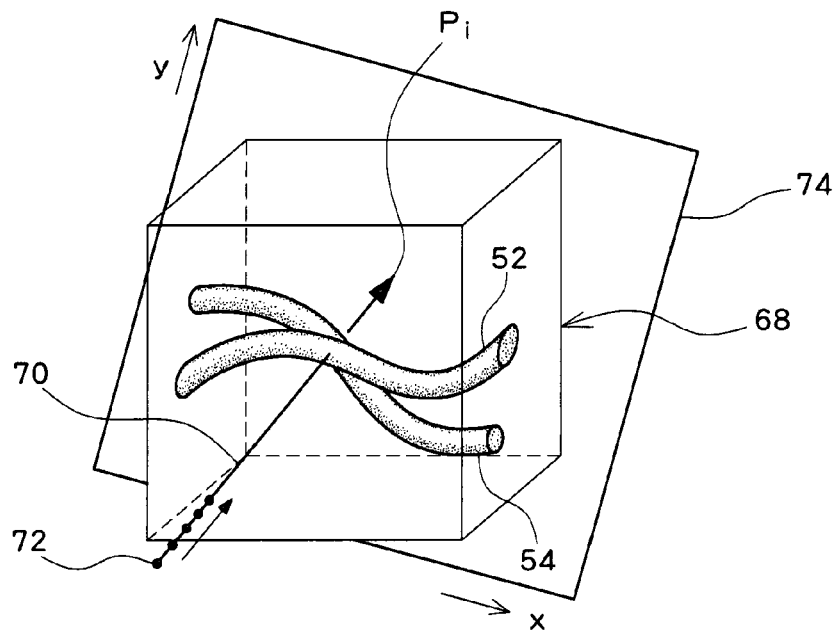
FIG. 3 is a conceptual view for explaining a relationship between the bloodstream volume data and a screen.
Figure 4:
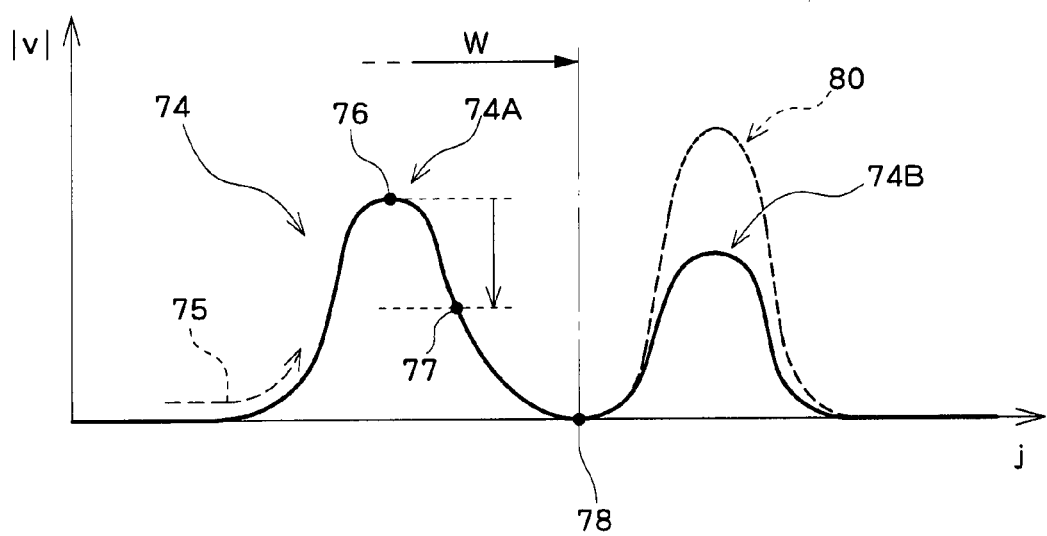
FIG. 4 is a chart (graph) showing distribution of voxel values along a ray.
Figure 5:
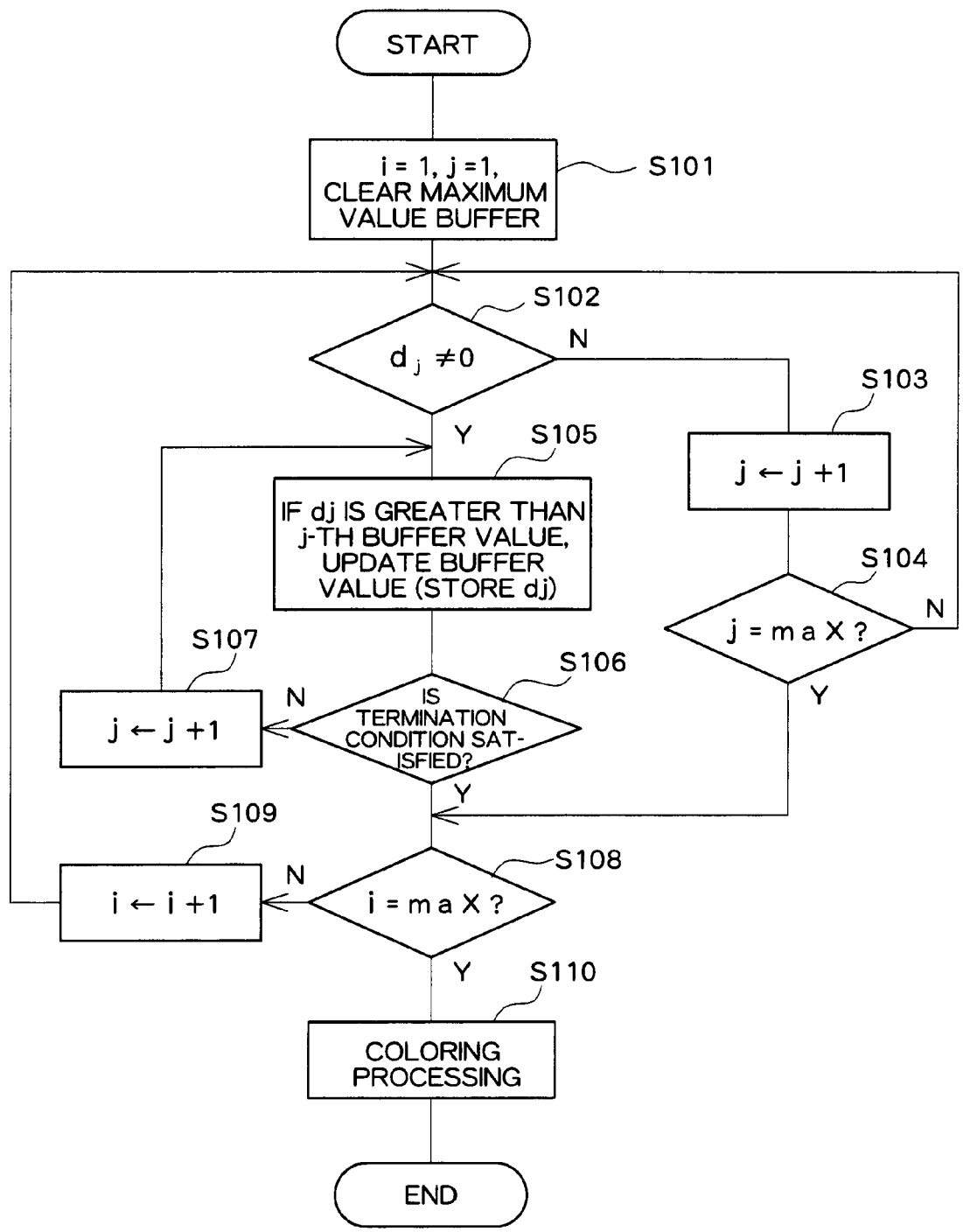
FIG. 5 is a flowchart showing processing for forming a three-dimensional bloodstream image.

Referring now to FIGS. 3 to 5, processing for forming a three-dimensional bloodstream image will be described.

FIG. 3 shows the bloodstream volume data 68. A modified maximum value detection method, which will be described below, is to be applied to the bloodstream volume data 68. First, a plurality of virtual rays (lines of sight) are set with respect to the bloodstream volume data 68. Here, a viewpoint 72 can be set at an arbitrary position. In the example shown in FIG. 3, only one representative ray 70 is shown. The plurality of rays may be parallel to each other or non-parallel. For each ray, an operation which will be described below is executed to determine one pixel value. By mapping, on a screen 74, a plurality of pixel values which are obtained for the plurality of rays, a three-dimensional bloodstream image can be formed.

Now, with regard to the ray 70, voxel values are sequentially obtained in the order of voxels on the ray 70, starting from the viewpoint 72. Namely, a maximum value search processing is executed. Here, it is desired that the voxel value is an absolute value of the velocity, in order to specify the bloodstream on the front side, regardless of the direction of the stream (i.e. regardless of a negative sign or a positive sign). In the example shown in FIG. 3, the ray 70 penetrates both the portion 52 corresponding to a bloodstream and the portion 54 corresponding to a bloodstream, and is associated with a specific address Pi on the screen 74.

FIG. 4 shows, in a graph, a sequence of voxel values existing on the ray described above. The left end of the horizontal axis represents the viewpoint or a search start point, and the direction to the right from the viewpoint represents the depth direction. Further, the vertical axis represents the magnitude of a voxel value, which is an absolute value of the velocity in the present embodiment. Specifically, although, in the actual display of an image, each bloodstream is represented with a hue in accordance with the direction of the stream in consideration the positive or negative sign, the sign should not be considered when specifying the peak of the bloodstream located on the front side, and therefore an absolute value of the velocity is referred to. Here, when the voxel value corresponds to a power, the voxel value is directly referred to for performing search of the maximum value.

The graph shown in FIG. 4 includes two hills 74A and 74B. The first hill 74A corresponds to the bloodstream 52 located on the front side in FIG. 3, and the following hill 74B corresponds to the bloodstream 54 located on the further back side in FIG. 3. Once search of the maximum value is started from the search start point, the voxel values are sequentially referred to along the j direction or the depth direction as indicated by reference numeral 75. Then, as will be described below with reference to FIG. 5, the current voxel value which is being referred to is compared with the current maximum value stored in a buffer. If the current voxel value is greater than the current maximum value, the maximum value stored in the buffer is updated; i.e., the current voxel value is written in the buffer. With sequential repetition of this processing, after the voxel value of the first peak 76 corresponding to the vertex of the first hill 74A is stored in the buffer, the buffer value remains unupdated, and the reference position descends a slope of the hill 74A.

In the present embodiment, if the voxel value increases and then decreases to finally reach 0 in the course of search; i.e., if the voxel value reaches a point indicated by reference numeral 78, the maximum value search processing is completed. At this point in time, the maximum value currently stored in the buffer is identified as a specific maximum value, and is then converted into a pixel value. In this shown example, the value of the first peak 76 is identified as the specific maximum value.

Accordingly, the second hill 74B is not considered as a search subject, because the search is completed before the second hill 74B. Consequently, in the portion in which the two bloodstreams cross each other, only the bloodstream located on the front side is displayed, thereby avoiding a problem that the bloodstream on the further back side is unnecessarily imaged.

Although in the present embodiment, the search is completed at the time point when the first hill is crossed to find the first valley, the search may be completed at a position 77 located at a predetermined level further down from the peak 76, for example. Alternatively, it is also possible to compute a gradient at each point and terminate the search at a point where the current gradient exceeds a predetermined value.

The present embodiment can provide an advantage that even if a second hill 80 is higher than the first hill 74A, the first peak 76, which is the vertex of the first hill 74A, can be specified reliably. However, the second or subsequent hill may be referred to for the purpose of preventing misidentification of the peak.

FIG. 5 shows, in a flowchart, a processing for forming a three-dimensional bloodstream image. First, in step S101, 1 is set as i, which represents a ray number, and also 1 is set as j, which represents a step number on the ray; i.e., a voxel address. Also, a maximum value buffer is cleared. In step S102, whether or not a currently-referred voxel value dj is 0 is determined. If dj is 0, the voxel which is currently being referred to is assumed to be located on the front side with respect to the first bloodstream. Then, in step S103, j is incremented by 1, and in step S104, whether or not j is a maximum value is determined. If j is determined to be a maximum value, processing in step S108 is executed in order to terminate the processing with regard to the ray which is currently noted. On the other hand, if j is not determined to be a maximum value in step S104, the processing proceeds to step S102.

If in step S102 it is determined that the voxel value dj is not 0, the processing in step S105 is performed. More specifically, a determination is made as to whether or not the voxel value dj which is currently being noted is greater than the j-th buffer value corresponding to the currently-noted ray. If the currently-noted voxel value dj is greater, there is executed update processing in which the current buffer value is replaced by the currently-noted voxel value dj. If the voxel value dj is equal to or smaller than the current buffer value, such update processing is not performed.

In step S106, whether or not a termination condition is satisfied is determined with regard to the current ray. As shown in FIG. 4, when the first hill is crossed and then the voxel value 0 is reached, it is determined that the termination condition is satisfied. Alternatively, other termination conditions may be applied. If the termination condition is not satisfied, processing proceeds to step S107, in which j is incremented by 1, and then step S105 and the subsequent steps are repeated. On the other hand, if it is determined that the termination condition is satisfied with regard to the currently-noted ray, then, in step S108, whether or not i, which is a ray number, reaches a maximum value is determined. Then, if it is determined that i does not reach the maximum value, i is incremented by 1 in step S109, and then step S102 and the subsequent steps described above are repeated.

On the other hand, if in step S108 it is determined that i reaches a maximum value, in step S110, coloring processing is applied to a three-dimensional bloodstream image formed of a plurality of pixel values which have been obtained until then. More specifically, hue and brightness are assigned in accordance with the direction and magnitude of the velocity, so that a three-dimensional bloodstream image, which is a color image, is formed.

In the three-dimensional bloodstream image, as described above with reference to FIG. 3, in a portion in which the bloodstreams cross each other, the bloodstream located on the front side seen from the viewpoint is preferentially displayed. In addition, when displaying each bloodstream, a center portion of the bloodstream with a higher velocity is displayed with a higher priority than a peripheral portion around the center portion of the bloodstream with a lower velocity, so that each bloodstream can be clearly displayed with a sense of depth. Further, with the above processing, high-speed computation can be executed, because the computation concerning the subject ray is completed if the first peak is specified and then the termination condition is satisfied. Although it is possible to apply weighting processing along the depth direction so as to prevent the bloodstream located on the deeper side from being displayed preferentially, such special and additional processing is not necessary according to the structure of the present embodiment. However, such a weighting processing in the depth direction may be performed for the purpose of image adjustment and so on.

As described above, the ultrasound diagnostic apparatus according to the present embodiment can advantageously generate bloodstream volume data in which noises (particularly clutter) present in a three-dimensional space are removed, and can further advantageously form a three-dimensional bloodstream image which is based on such bloodstream volume data and which also can provide a sense of depth and can faithfully represent motion information. The ultrasound diagnostic apparatus according to the present embodiment has two characteristics features (noise removal based on the object size, and image processing for preferentially displaying the bloodstream on the front side), which can be adopted independently from each other. It is possible, for example, to first generate the bloodstream volume data using the method as shown in FIG. 2, and then apply various known volume rendering methods to the bloodstream volume data. It is also possible to generate bloodstream volume data by using a general method and then apply the method described in FIGS. 3 to 5 to preferentially display the bloodstream located on the front side.

Although the preferred embodiment of the present invention has been described using specific terms, such description is for illustrative purposes only, and it is to be understood that changes and variations may be made without departing from the spirit or scope of the appended claims.

What is claimed is:

1. An ultrasound diagnostic apparatus, comprising:
a unit which transmits and receives ultrasonic waves with respect to a three-dimensional space within a living organism to obtain original volume data;
a computation unit which extracts motion information from the original volume data to generate motion volume data;
an identification unit which specifies a plurality of objects included in the motion volume data and identifies a type of each of the objects which are specified to thereby generate, as identification data, three-dimensional mask data for identifying a noise portion in the motion volume data;
an extraction unit which extracts bloodstream volume data from the motion volume data, the extraction unit having a three-dimensional gate-processing unit which removes the noise portion in the motion volume data by performing a logical operation between the three-dimensional mask data and the motion volume data; and
an image-forming unit which forms a three-dimensional bloodstream image by reference to the bloodstream volume data.

2. The ultrasound diagnostic apparatus according to claim 1, wherein
the identification unit identifies the type of an object by reference to the size of each of the objects which are specified.

3. The ultrasound diagnostic apparatus according to claim 1, wherein
the identification unit further includes a labeling processing unit which applies three-dimensional labeling processing to the motion volume data to thereby specify the plurality of objects.

4. The ultrasound diagnostic apparatus according to claim 3, wherein
the identification unit further includes a determination unit which determines whether or not each object is a bloodstream, by reference to a three-dimensional volume size of each object.

5. The ultrasound diagnostic apparatus according to claim 4, wherein the three-dimensional volume size of the object is determined by counting a number of voxels the object comprises.

6. The ultrasound diagnostic apparatus according to claim 3, wherein
the identification unit further includes a binarization processing unit which applies binarization processing to the motion volume data prior to the three-dimensional labeling processing, and
the volume data having been subjected to the binarization processing are input to the labeling processing unit.

7. The ultrasound diagnostic apparatus according to claim 6, wherein
the binarization processing unit compares each of voxel data items forming the motion volume data with a discrimination reference value to thereby convert each of voxel data items into a valid value or an invalid value.

8. The ultrasound diagnostic apparatus according to claim 1, wherein
the identification unit identifies an object which is greater than a predetermined size as a bloodstream and identifies an object which is smaller than the predetermined size as noise which is not a bloodstream.

9. The ultrasound diagnostic apparatus according to claim 1, wherein
the image-forming unit sets a plurality of rays with respect to the bloodstream volume data to thereby determine a pixel value based on a sequence of voxel data on each ray.

10. The ultrasound diagnostic apparatus according to claim 9, wherein
the image-forming unit determines a pixel value concerning each ray by means of a maximum value method.

11. The ultrasound diagnostic apparatus according to claim 10, wherein
the image-forming unit assumes a first peak on each ray as a maximum value.

12. The ultrasound diagnostic apparatus according to claim 11, wherein
the first peak corresponds to a velocity or a power at a center portion of a bloodstream located on the front side closest to a viewpoint.

13. The ultrasound diagnostic apparatus according to claim 1, wherein
the motion information is velocity information or power information, and
the motion volume data are composed of the motion information corresponding to the three-dimensional space.

14. The ultrasound diagnostic apparatus according to claim 1, wherein
the three-dimensional bloodstream image is a color image.

15. The ultrasound diagnostic apparatus according to claim 1, further including:
a further image-forming unit which forms a three-dimensional tissue image by reference to the original volume data; and
a display unit which displays the three-dimensional bloodstream image and the three-dimensional tissue image.

16. A method of forming a three-dimensional bloodstream image by referencing motion volume data and executed by a computer, the method comprising:
specifying a plurality of objects included in the motion volume data and determines whether or not each of the objects which are specified is a bloodstream to thereby generate as identification data, three-dimensional mask data for identifying a noise portion in the motion volume data;
extracting bloodstream volume data from the motion volume data by reference to the identification data,
wherein during extraction a three-dimensional gate-processing unit removes the noise portion in the motion volume data by performing a logical operation between the three-dimensional mask data and the motion volume data; and
forming a three-dimensional bloodstream image by reference to the bloodstream volume data.

* * * * *